(12) United States Patent
Chander

(10) Patent No.: US 10,332,410 B2
(45) Date of Patent: Jun. 25, 2019

(54) HEALTHCARE SYSTEM TO CHANGE BEHAVIOR OF A USER

(71) Applicant: FUJITSU LIMITED, Kawasaki-shi, Kanagawa (JP)

(72) Inventor: Ajay Chander, San Francisco, CA (US)

(73) Assignee: FUJITSU LIMITED, Kawasaki (JP)

( * ) Notice: Subject to any disclaimer, the term of this patent is extended or adjusted under 35 U.S.C. 154(b) by 700 days.

(21) Appl. No.: 15/013,942

(22) Filed: Feb. 2, 2016

(65) Prior Publication Data

US 2017/0221370 A1 Aug. 3, 2017

(51) Int. Cl.
| | |
|---|---|
| *G09B 5/02* | (2006.01) |
| *G16H 20/60* | (2018.01) |
| *G06Q 40/08* | (2012.01) |
| *G06Q 20/40* | (2012.01) |
| *G09B 19/00* | (2006.01) |

(52) U.S. Cl.
CPC ............ *G09B 5/02* (2013.01); *G06Q 20/407* (2013.01); *G06Q 40/08* (2013.01); *G09B 19/0092* (2013.01); *G16H 20/60* (2018.01)

(58) Field of Classification Search
CPC ...... G09B 5/02; G09B 19/0092; G16H 20/06; G06F 19/00; G06Q 40/08; G06Q 20/407
See application file for complete search history.

(56) References Cited

U.S. PATENT DOCUMENTS

| | | | | |
|---|---|---|---|---|
| 2008/0146334 | A1* | 6/2008 | Kil | G06Q 40/08 463/36 |
| 2008/0146892 | A1* | 6/2008 | LeBoeuf | G16H 50/30 600/300 |
| 2011/0191158 | A1* | 8/2011 | Kateraas | G06F 19/3418 705/14.27 |
| 2014/0156308 | A1* | 6/2014 | Ohnemus | G06F 19/3418 705/3 |
| 2014/0164013 | A1* | 6/2014 | Schwarzberg | G06F 19/3475 705/2 |

(Continued)

OTHER PUBLICATIONS

Stickk.com, Launched Jan. 2008, Retrieved on Feb. 2, 2016, Retrieved from <http://www.stickk.com/>.

(Continued)

*Primary Examiner* — Robert T Clarke, Jr.
(74) *Attorney, Agent, or Firm* — Maschoff Brennan

(57) ABSTRACT

A method to change a behavior of a user includes receiving state data indicative of a current state of a user. The method includes receiving sensor data generated by one or more sensors, the sensor data indicative of one or more behaviors of the user. The method includes receiving payment from the user to purchase a virtual attribute, at least a portion of the payment to be returned to the user responsive to an improvement to the one or more behaviors over an earn-back time period. The method includes determining a behavior-based virtual attribute of the user based on the sensor data. The method includes estimating a future state of the user from the current state of the user, the behavior-based virtual attribute, and the purchased virtual attribute. The method includes generating graphical data including a visualization of the future state of the user to display to the user.

20 Claims, 8 Drawing Sheets

(56) References Cited

U.S. PATENT DOCUMENTS

| | | | |
|---|---|---|---|
| 2015/0064671 A1* | 3/2015 | Murville | G09B 5/00 |
| | | | 434/236 |
| 2016/0012194 A1* | 1/2016 | Prakash | G06F 19/00 |
| | | | 705/2 |
| 2016/0171180 A1* | 6/2016 | Yagnyamurthy | G06F 19/36 |
| | | | 705/3 |

OTHER PUBLICATIONS

Dietbet.com; Retrieved on Feb. 2, 2016, Retrieved from <https://www.dietbet.com/>.

Kim Kardashian: Hollywood video game, Retrieved on Feb. 2, 2016, Retrieved from <https://play.google.com/store/apps/details?id=com.glu.stardomkim&hl=en>.

Kahneman D. and Amos Tversky, "Choices, Values, and Frames," The American Psychologist Association, Inc., vol. 39, No. 4, p. 341-350, Apr. 1984.

Hershfield, Hal E. et al., "Increasing Saving Behavior Through Age-Progressed Renderings of the Future Self," Journal of Marketing Research vol. 48: Nov. 2011, S23-S37.

* cited by examiner

HEALTHCARE SYSTEM TO CHANGE BEHAVIOR OF A USER

FIELD

The embodiments discussed herein are related to a healthcare system to change behavior of a user.

BACKGROUND

Behavior is notoriously hard for people to change, even if it makes rational sense for people to act in a particular manner. For example, people with type 2 diabetes may improve their condition and in some cases even reverse the type 2 diabetes through diet and exercise. However, in many cases people with type 2 diabetes prefer to take drugs with possible side effects rather than make behavior changes.

The subject matter claimed herein is not limited to embodiments that solve any disadvantages or that operate only in environments such as those described above. Rather, this background is only provided to illustrate one example technology area where some embodiments described herein may be practiced.

SUMMARY

According to an aspect of an embodiment, a method to change behavior of a user includes receiving state data indicative of a current state of the user. The method also includes receiving sensor data generated by one or more sensors, the sensor data indicative of one or more behaviors of the user. The method also includes receiving payment from the user to purchase a virtual attribute, at least a portion of the payment to be returned to the user responsive to an improvement to the one or more behaviors over an earn-back time period. The method also includes determining a behavior-based virtual attribute of the user based on the sensor data. The method also includes estimating a future state of the user from the current state of the user, the behavior-based virtual attribute, and the purchased virtual attribute. The method also includes generating graphical data including a visualization of the future state of the user to display to the user.

The object and advantages of the embodiments will be realized and achieved at least by the elements, features, and combinations particularly pointed out in the claims.

It is to be understood that both the foregoing general description and the following detailed description are exemplary and explanatory and are not restrictive of the invention, as claimed.

BRIEF DESCRIPTION OF THE DRAWINGS

Example embodiments will be described and explained with additional specificity and detail through the use of the accompanying drawings in which.

DESCRIPTION OF EMBODIMENTS

Figure 1:
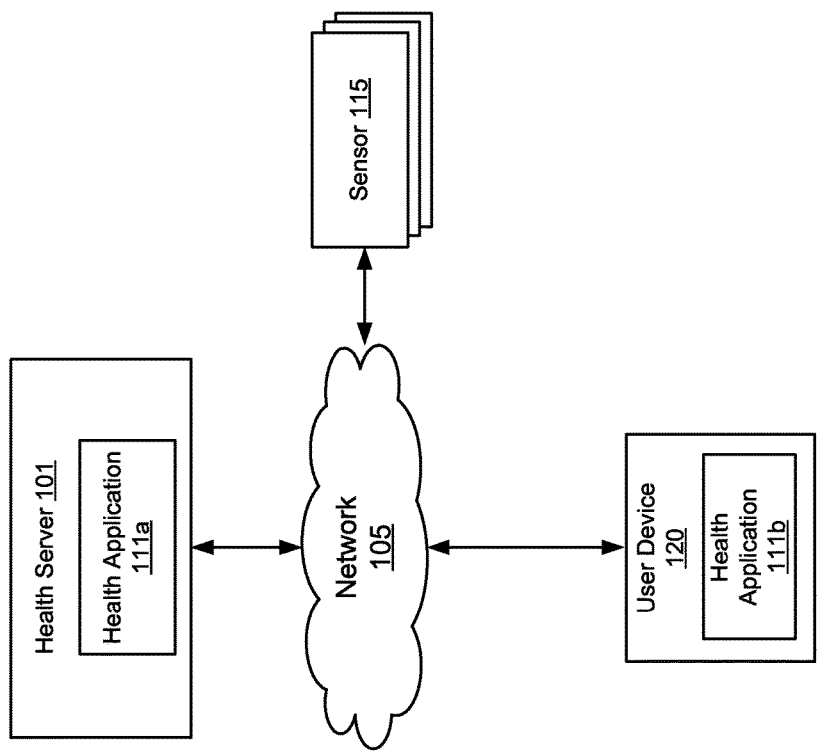
FIG. 1 is a block diagram of an example health system configured to change behavior of a user.

Research shows that people may be willing to change their behavior if faced with potential loss. For example, people may take more steps to avoid losing $5 than they would be willing to take to obtain $5. Loss-aversion applications exist to encourage users to reach their goals. For example, some loss-aversion applications receive money from users to reach a goal. If the users fail to meet the goal, the money may be forfeited.

Similarly, some people may be willing to change their behavior if they are able to visualize their future selves prior to considering a particular decision. For example, people may be more likely to save towards retirement after viewing age-processed renderings or after viewing graphs or narrative descriptions or other data that indicate monthly disposable income under certain one or more saving/retirement plans.

In comparison, some embodiments described herein may use both loss aversion and visualizations to encourage a user to change behavior. The health system described herein may include a computing device. For example, the health system may include a personal computer, laptop, tablet computer, mobile telephone, server, or any processor-based computing device. The health system may include a memory and a processor device. The processor device may be programmed to perform or control performance of one or more operations described herein, such as one or more operations or steps of method 500 described below with reference to FIG. 5. One or more example embodiments of the health system are described below.

The health system may include a health application that receives state data indicative of a current state of a user. For example, the state data may indicate that the user weighs 170 pounds. The health application may receive sensor data generated by one or more sensors. For example, the sensor data may include step data from a pedometer and calories consumed by the user from a calorie counting application. The sensor data may be indicative of one or more behaviors of the user. For example, the sensor data may indicate that the user averages 6,000 steps per day and consumes an average of 3,000 calories per day.

The health application may receive a payment from the user to purchase a virtual attribute where at least a portion of the payment may be returned to the user responsive to an improvement to the one or more behaviors over an earn-back time period. For example, the user may provide a $15 payment for a three-pound weight reduction. The earn-back time period may be specified by the user, for example, the user may specify that the earn-back time period is one month. Continuing with the example above, the improvement to the one or more behaviors over the earn-back time period may include an increase to the user's number of steps, a decrease in the number of calories consumed, or a combination of both increased steps and decreased calorie consumption.

The health application may determine a behavior-based virtual attribute based on the sensor data by, e.g., applying a behavior-based virtual attribute rule to the sensor data. For example, the sensor data may indicate the user's average daily steps for the last month or more, which may be used to determine the user's behavior-based virtual attribute. The one or more behavior-based virtual attribute rules applied by the health application may specify that an average daily number of steps for a month that exceeds (or is less than) a baseline number of steps and/or that exhibits at least a threshold improvement (or worsens) from one month to the next results in a particular behavior-based virtual attribute. In this example, the behavior-based virtual attribute may include weight reduction (or gain) with a value that may depend on, e.g., how much the baseline is exceeded (or the opposite). As another example, the behavior-based virtual attribute rules may depend on the user's average daily caloric consumption, or some other behavior indicated by the sensor data. In some embodiments, behavior-based virtual attribute rules may generally map one or more particular behaviors over one or more particular periods (e.g., average daily number of steps for a month, average daily caloric consumption for a month) and/or changes thereof from one period to the next to one or more corresponding behavior-based virtual attributes and/or values thereof. Consistent with the examples already given, for instance, how much a particular behavior for a month exceeds (or is less than) a baseline or changes from one period to the next may map to a particular value of a corresponding behavior-based virtual attribute (e.g., virtual weight reduction or gain).

The health application may estimate a future state of the user from the current state of the user, the behavior-based virtual attribute, and the purchased virtual attribute. For example, the health application may estimate that the future state of the user will weigh five pounds less than the current state of the user based on the behavior-based virtual attribute being two pounds of weight loss and the purchased virtual attribute being three pounds of weight loss.

The health application may generate graphical data including a visualization of the future state of the user to display to the user. The visualization may generally include any data that helps a user form mental images or pictures of what the user may look like and/or other attributes the user may have in the future. The visualization may indicate what the user could look like if the user achieves the future state in the future. For example, the visualization of the future state could be a slimmed-down avatar of the user or a heavier avatar of the user, depending on, e.g., the user's current state, behavior (which is determinative of the user's behavior-based virtual attributes), and any purchased virtual attributes. Alternatively or additionally, the visualization may include a narrative description of future attributes for the user if the user achieves the future state. For example, the narrative description of future attributes may indicate that the user has better health including, e.g., a lower weight, a lower blood pressure, better cholesterol, and a longer life expectancy, or worse health depending on, e.g., the user's current state, behavior, and any purchased virtual attributes.

The described embodiments may provide improvements to healthcare, including improvements to, e.g., weight loss, heart health, and mental health, among potentially others. For instance, instead of, or in addition to, expensive doctor visits, pharmaceuticals, or surgeries to manage weight loss, heart health, and/or mental health, patients may manage weight loss, heart health, and/or mental health by leveraging both visualization and loss aversion according to the embodiments described herein. Alternatively or additionally, the embodiments described herein may effect the transformation of users, e.g., human users, from a current state of health to an improved state of health in which the users have a longer expected lifespan, lower health risk factors, and better quality of life, among potentially other health benefits.

Some embodiments will be explained with reference to the accompanying drawings. With respect to the use of substantially any plural and/or singular terms herein, those having skill in the art may translate from the plural to the singular and/or from the singular to the plural as is appropriate to the context and/or application. The various singular/plural permutations may be expressly set forth herein for sake of clarity.

FIG. 1 is a block diagram of an example health system 100 configured to change behavior of a user, arranged in accordance with at least some embodiments described herein. The health system 100 may include sensors 115, a health server 101, and a user device 120 that may communicate with each other via a network 105. One or more example implementations of the health system 100 are described below.

The network 105 may include one or more wide area networks (WANs) and/or local area networks (LANs) that may enable communication among the health server 101, the user device 120, and the sensors 115. In some embodiments, the network 105 includes the Internet, including a global internetwork formed by logical and physical connections between multiple WANs and/or LANs. Alternately or additionally, the network 105 may include one or more cellular radio frequency (RF) networks, global positioning system (GPS) networks, and/or one or more wired and/or wireless networks such as, but not limited to, 802.xx networks, Bluetooth access points, wireless access points, or internet protocol (IP)-based networks. The network 105 may also include servers that enable one type of network to interface with another type of network.

The sensors 115 may include hardware and/or applications that generate sensor data and transmit the sensor data over the network 105 to the health server 101 and/or the user device 120. The sensors 115 may also receive information from the health server 101 and/or the user device 120, such as a request for sensor data or information to configure how the sensor data may be formatted.

The sensors 115 that include hardware may include one or more of a pedometer, a scale, a sleep sensor, a location sensor (e.g. a GPS sensor), a blood pressure monitor, a pulse oximeter, a cholesterol monitoring device, a heart rate monitor, or an altimeter. The sensors 115 that include applications may include one or more of a calorie counting application, an exercise application, and a medical application that provides an electronic health record associated with a user. The medical application may include information generated by a doctor, a hospital, a laboratory, or another medical institution associated with a user.

The sensors 115 may be controlled by the user. For example, the user may wear a smart watch that includes a pedometer that measures the user's steps and a GPS sensor that determines the user's location. In another example, the user may use a calorie counting application to log foods and/or liquids that the user consumes during the day.

Additionally or alternatively, one or more of the sensors 115 may be controlled by an entity associated with the user. For example, the user may give a doctor permission to transmit the user's medical information to the health server 101 and/or the user device 120. This may be helpful for sensor data that the user may not easily obtain from other sources, such as the user's cholesterol level.

The health server 101 may include hardware (e.g., rack-mounted server computers, blade server computers, and/or other computer hardware) and/or applications. The health server 101 may include a memory and a processor device. The processor device may be programmed to perform or control performance of one or more operations described herein, such as one or more operations or steps of the method 500 described below with reference to FIG. 5.

The health server 101 may include a health application 111*a* that is configured to change a behavior of a user. For example, the health application 111*a* may receive state data indicative of a current state of a user. As one example, the state data may indicate that the user currently weighs 170 pounds. The state data may be received from one of the sensors 115 or the user may manually enter the state data. For example, where the state data includes a user's weight, the sensor 115 may include a scale that wirelessly transmits the user's weight to the health application 111*a* via the network. Alternatively, the user may manually input the user's weight via a user interface generated by the health application 111*a*.

The health application 111*a* may receive sensor data from one or more of the sensors 115. The health application 111*a* may use the sensor data to determine the user's behavior. For example, the sensor data may include information about how many steps the user has taken during the day (e.g., 6,000). The sensor data may include historical data that the health application 111*a* uses to determine the user's historical behavior, e.g., to be used for comparison purposes. For example, the health application 111*a* may determine that the user's average daily number of steps have increased 12% since last month.

The health application 111*a* may receive a payment from the user to purchase a virtual attribute. For example, the health application 111*a* may receive a $15 payment from the user to lose three pounds where each pound costs $5. The health application 111*a* may return at least a portion of the payment to the user if the user improves upon the behavior over an earn-back time period. For example, the user may define the earn-back time period as one month or some other duration of time. The payment may be returned to the user, in whole or in part, at the end of the earn-back time period contingent upon the user improving one or more behaviors. For instance, the health application 111*a* may determine that the user will receive a full value of the payment if the user increases an average daily number of steps by 500 steps in the earn-back time period or improves some other behavior (such as reducing average daily caloric consumption).

Accordingly, in some embodiments, at an end of the earn-back time period the health application 111*a* may determine an improvement for the user based on a specific change in the behavior and may use the improvement to determine a value of the payment to return to the user. Continuing with the example above, if the health application 111*a* determines at the end of the earn-back time period that the user has increased the average daily number of steps by 500, the user may receive the full $15 payment back. If the health application 111*a* determines that the user increased the average daily number of steps by less than 500, the returned payment may be prorated. For instance, if it is determined that the user increased the average daily number of steps by 400 (which is 80% of 500), the user may receive a $12 payment (which is 80% of $15). If it is determined that the user fails to increase the average number of steps at all and/or if the average number of steps decreases, the user may forfeit the entire $15 payment.

The health application 111*a* may determine a behavior-based virtual attribute based on the sensor data at any time, such as at the beginning of the earn-back time period and/or at the end of the earn-back time period or at any other time. The behavior-based virtual attribute may be determined by the health application 111*a* applying one or more behavior-based virtual attribute rules to the sensor data. In general, each behavior-based virtual attribute rule may specify a relation between behavior of the user (as indicated by the sensor data) and a behavior-based virtual attribute (and/or its value). Specific examples of behavior-based virtual attributes may include weight change, blood pressure change, heart rate change, cholesterol level change, or a change to a fitness measurement. In an example embodiment, the health application 111*a* may apply two behavior-based virtual attribute rules to determine that the behavior-based virtual attribute includes a 1-pound weight loss when the sensor data indicates that the user's average daily steps are 6000 steps per day and an additional 1-pound weight loss when the sensor data indicates that the user's average daily steps have increased more than 10% since a preceding month. In this example, the health application 111*a* may therefore determine that the behavior-based virtual attribute is a total weight loss of two pounds.

The health application 111*a* may estimate a future state of the user from the current state of the user, the behavior-based virtual attribute, and the purchased virtual attribute. For example, the health application 111*a* may estimate that the user's current state is 170 pounds, the behavior-based virtual attribute is two pounds of weight loss, and the purchased virtual attribute is three pounds of weight loss. The health application 111*a* may generate graphical data including a motivational visualization of the future state of the user to display to the user. For example, the health application 111*a* may generate a motivational visualization of the user after a total five-pound weight loss to inspire the user to continue improving upon the user's behavior.

The user device 120 may include a memory and a processor, and may be implemented as, for example, a desktop computer, a laptop computer, a tablet computer, a mobile telephone, a personal digital assistant (PDA), a mobile e-mail device, a portable game player, a portable music player, a mobile device, a wearable device, a smart watch, or other electronic device capable of accessing the network 105.

The user device 120 may include a health application 111*b*. The health application 111*b* may include the same or similar components as the health application 111*a* or different components or a different combination of components. The health application 111*b* may act as a thin-client application that may be stored in part on the user device 120 and in part on the health server 101. For example, the health application 111*b* may receive instructions from the health application 111*a* to generate graphical data for display on the user device 120. Alternatively or additionally, the health application 111*b* may accept payments for virtual attributes. In another embodiment, the health application 111*b* may perform all the functions of the health application 111*a* and send information to the health application 111*a* for remote storage. In some embodiments, a user accesses the health application 111*a* instead of the health application 111*b*, for example, by accessing the health application 111*a* via a browser. The health application stored on either the health server 101 or the user device 120 may be referred to generally as "health application 111."

In some embodiments, the user device 120 may include one of the sensors 115. For example, the user device 120 may include a mobile device, a smart watch, or a wearable device that includes a calorie counting application and a pedometer. As a result, in some embodiments the health application 111 receives sensor data from sensors 115 and/or applications that are part of the user device 120 instead of over the network 105.

Figure 2:
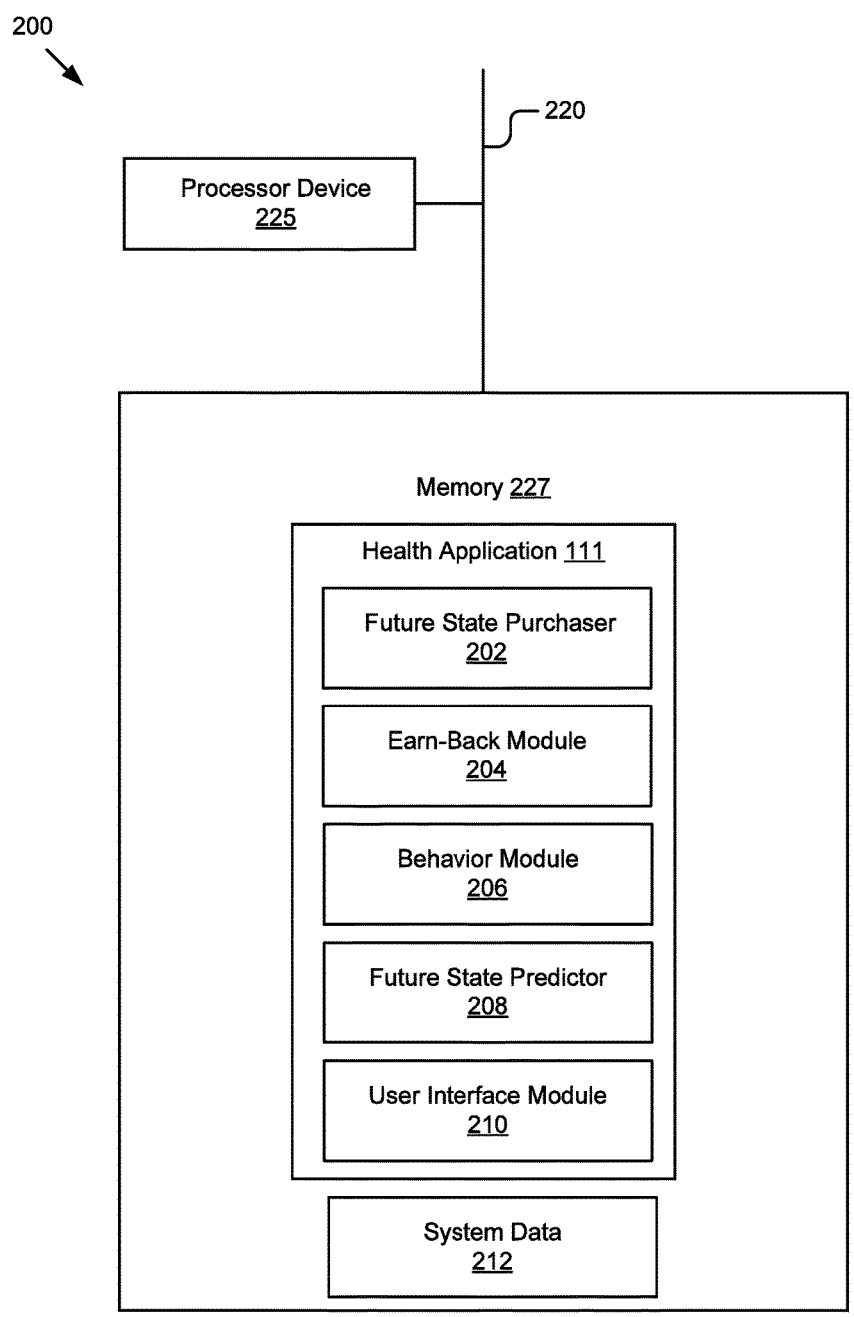
FIG. 2 illustrates an example device to change behavior of a user.

FIG. 2 illustrates an example device 200 to change behavior of a user. The device 200 of FIG. 2 may be an example of hardware used by the health system 100 described above with reference to FIG. 1. The device 200 may include a special purpose processor-based computing device programmed to perform one or more blocks of the method 500 described below with reference to FIG. 5. The device 200 may correspond to or include one or more of the health server 101 or the user device 120 of FIG. 1.

The device 200 may include a processor device 225 and a memory 227. The processor device 225 may include an arithmetic logic unit, a microprocessor, a general-purpose controller, or some other processor or processor array to perform or control performance of operations as described herein. The processor device 225 processes data signals and may include various computing architectures including a complex instruction set computer (CISC) architecture, a reduced instruction set computer (RISC) architecture, or an architecture implementing a combination of instruction sets. Although FIG. 2 illustrates a single processor device 225, the device 200 may include multiple processor devices 225. Other processors, operating systems, and physical configurations may be possible.

The memory 227 stores instructions or data that may be executed or operated on by the processor device 225. The instructions or data may include programming code that may be executed by the processor device 225 to perform or control performance of the operations described herein. The memory 227 may include a Dynamic Random Access Memory (DRAM) device, a Static Random Access Memory (SRAM) device, flash memory, or some other memory device. In some embodiments, the memory 227 also includes a non-volatile memory or similar permanent storage and media including a hard disk drive, a floppy disk drive, a Compact Disc-ROM (CD-ROM) device, a DVD-ROM device, a DVD-RAM device, a DVD-RW device, a flash memory device, or some other mass storage for storing information on a more permanent basis.

In the depicted embodiment, the memory 227 may store one or more of the health application 111 of FIG. 1 and system data 212. In some embodiments, the health application 111 may be implemented using hardware including a field-programmable gate array (FPGA) or an application-specific integrated circuit (ASIC). In some other embodiments, the health application 111 may be implemented using a combination of hardware and software.

The health application 111 may include a future state purchaser 202, an earn-back module 204, a behavior module 206, a future state predictor 208, and a user interface module 210. While the modules 202, 204, 206, 208, and 210 are illustrated as being stored on one device 200, the modules 202, 204, 206, 208, and 210 may be stored on different devices, for example, in a distributed data system.

The system data 212 may include data used by the device 200 to provide its functionality. For example, the system data 212 may include one or more of state data, sensor data (including historical data), purchase information for virtual attributes, earn-back rules, behavior-based virtual attribute rules, a proration policy, rules that specify costs—in terms of sensor data—to earn back payments for purchased virtual attributes, user data including images uploaded by the user, and graphical data.

The various modules 202, 204, 206, 208, and 210 of the health application 111 will now be described in more detail.

The future state purchaser 202 may define a list of virtual attributes that the user may purchase and/or may receive a payment from the user to purchase a virtual attribute. The future state purchaser 202 may specify a cost per unit, in terms of money, of each of the virtual attributes. Alternatively or additionally, the user may create a new type of virtual attribute. The purchased virtual attributes may include, for example, a weight change, a blood pressure change, a heart rate change, a cholesterol level change, a change to a length of time since the user last had a panic attack, or a change to a fitness measurement, such as a time to run a mile, a distance to swim, a time to perform an activity, etc. In some embodiments, the virtual attribute may include a package of purchased virtual attributes. The package of purchased virtual attributes may be aimed at improving a health condition. For example, a cardiovascular health package may include virtual attributes associated with cardiovascular health. The virtual attributes included in the cardiovascular health package may include weight loss, blood pressure reduction, and cholesterol level improvement. In this example, a current state of the user might include the user's current weight, current blood pressure, and current cholesterol levels, which may be respectively indicated by sensor data from a scale, sensor data from a blood-pressure monitor, and sensor data from a laboratory. The scale, blood-pressure monitor, and laboratory may be included in the sensors 115 of FIG. 1.

The future state purchaser 202 may instruct the user interface module 210 to generate graphical data to display one or more of the virtual attributes (e.g., a list of the virtual attributes), a cost per unit—in terms of money—of the virtual attribute, a number of units of the virtual attribute for the user to purchase, and information for providing payment information. The future state purchaser 202 may receive the payment in response to the user providing payment information via a user interface.

The future state purchaser 202 may keep the payment of the user until an end of an earn-back time period. After the earn-back time period ends, if the user fails to improve upon one or more behaviors associated with earning back the payment, some or all of the payment may be forfeited. The payment or a portion thereof may become profit for the developer of the health application 111, may be donated to charity, and/or may become part of a pool to pay users as a reward for changing their behavior. In some embodiments, after the earn-back time period ends, a new earn-back time period may begin. If the user improves upon the behavior during the new earn-back time period, some or all of the payment may be returned to the user after the new earn-back time period ends and/or at a discounted rate. Alternatively or additionally, some or all of the payment may be returned to the user incrementally during the earn-back time period and/or during the new earn-back time period.

The earn-back module 204 may determine an earn-back time period, receive sensor data generated by sensors 115, determine a cost, in terms of the sensor data for a user to earn back an amount of a payment associated with a purchased virtual attribute, determine a behavior change of the user that contributes to an improvement of one or more behaviors associated with earning back the payment, and determine whether to return all of the payment or a pro-rated portion of the payment to the user.

The earn-back time period may be assigned by the earn-back module 204 or defined by the user. For example, the earn-back time period may be one week, one month, one year, etc. The earn-back time period may be a relatively short amount of time so that the user may stay focused on changing a behavior or a relatively long period of time so that the user may maintain a consistent behavior change. In some embodiments, the earn-back time period may include multiple iterations where a user may earn-back a portion of the payment. For example, where the earn-back period is four months, it may be divided into four one-month intervals in which one quarter of the payment may be earned back each month.

In some embodiments, the earn-back time period may include a proration policy that describes how much of the payment is to be returned by the earn-back module 204 to the user. The proration policy may include a percentage of the payment based on a ratio between an actual behavior change as compared to a behavior change determined by the behavior module 206. The proration policy may be applied or executed by the earn-back module 204. Alternatively or additionally, the proration policy may be generated by the earn-back module 204. In some embodiments, the proration policy may be different depending on the earn-back time period. For example, the earn-back module 204 may generate a proration policy for a 1-month earn-back time period where the user recovers at least portion of the payment if the user has shown any improvement and a proration policy for a one-year earn-back time period where the user may not recover a portion of the payment unless the user has shown at least a 50% improvement. Alternatively, one or more pre-existing proration policies may be stored in system data 212 and the earn-back module 204 may apply or execute a corresponding one of the pre-existing proration policies.

The earn-back module 204 may receive sensor data generated by one or more sensors 115. The earn-back module 204 may use the sensor data to determine an actual behavior change of a user during or at the end of an earn-back time period to calculate an amount of a corresponding payment to return to the user.

The earn-back module 204 may determine a cost, in terms of sensor data generated by the one more sensors 115, for a user to earn back an amount of a payment for a purchased virtual attribute based on a default setting or customized information for the user. In general, the sensor data may indicate one or more behaviors of a user and/or one or more actual behavior changes when considered over time. Thus, the cost in terms of sensor data may be a proxy for a cost in terms of a behavior change of the user and the two costs may be used interchangeably. For example, the earn-back module 204 may determine that all users may need to walk an additional 1,000 steps per day for a week (as indicated by sensor data) to burn one pound based on an average user weighing 160 pounds. Alternatively, the earn-back module 204 may determine how many steps a user may need to walk to burn one pound based on the user's actual weight. For example, if a user weighs 200 pounds, the earn-back module 204 may determine that the user needs to walk an additional 900 steps per day for a week to burn one pound. In the foregoing examples, the additional steps per day for a week or other period (or other behavior change) is an example of a cost in terms of behavior change and the sensor data that indicates the additional steps per day for a week (or other behavior change) is an example of a cost in terms of sensor data.

The system data 212 may include various rules that specify the cost, in terms of sensor data, for the user to earn back an amount of payment associated with one unit of the virtual attribute. Accordingly, the earn-back module 204 may determine the cost, in terms of sensor data, by querying such rules in the system data 212.

The earn-back module 204 may determine a behavior change of the user that contributes to an improvement of a behavior associated with earning back the payment, e.g., the behavior change corresponding to the cost in terms of sensor data. This behavior change may in some cases be referred to as a target behavior change. The target behavior change may result in the user earning back a portion of the payment over the earn-back time period, all of the payment over the earn-back time period, or none of the payment over the earn-back time period. For example, where the behavior of the user includes an average 6,000 steps per day (e.g., for the last month), the earn-back module 204 may determine that the target behavior change for the user to earn back all of the payment is an average increase of 500 steps per day for a month.

The earn-back module 204 may receive sensor data generated by sensors 115 that is indicative of an actual behavior change of the user that contributes to the improvement to the behavior that is associated with earning back the payment. Continuing with the example above, the earn-back module 204 may determine the actual behavior change is an average increase of 400 steps per day for an average daily total of 6,400 steps.

The earn-back module 204 may determine an amount of the payment to return to the user based on the target behavior change and the actual behavior change. Determining the amount of the payment to return may include determining a ratio of the actual behavior change to the target behavior change and determining a value of the portion of the payment based on the ratio. For example, the earn-back module 204 may determine that where the ratio is one, the actual behavior change is greater than or equal to the target behavior change, where the ratio is between zero and one, the actual behavior change is less than the target behavior change, and the value based on the ratio may be determined by multiplying the payment by the ratio. As a concrete example, suppose the user is informed that $15 paid for three pounds of weight loss (which is an example of three units of a virtual attribute) can be earned back for an additional 500 steps per day (which is an example of a cost, in terms of sensor data (or target behavior change)) on average for a month (which is an example of an earn-back time period) and it is determined at the end of the month that the user's average daily steps for the month have only increased by 400 steps. The earn-back module 204 may determine in this example that a ratio of the actual behavior change to the target behavior change is 400/500, which is 0.80. The earn-back module 204 may then determine that the value of the portion of the payment based on the ratio and earned back by the user is 0.80*$15=$12.

In some embodiments, there may be multiple behaviors associated with earning back a payment for a purchased virtual attribute such that the amount of the payment earned back by the user may depend on multiple types of behavior changes. In the case of weight loss as a purchased virtual attribute, the multiple behavior changes associated with earning back the corresponding payment may include more steps, consumption of fewer calories, or obtaining more sleep each night. The earn-back module 204 may determine that at least one of the types of actual behavior changes was satisfied and thus contributed to the improvement of the behaviors and/or that a combination of types of actual behavior changes contributed to the improvement of the behaviors. For instance, the earn-back module 204 may determine that if the user averages an additional 500 steps per day or consumes an average of 1,000 calories less per day, or averages an additional hour of sleep per day, the user may receive all of the payment. Alternatively, the earn-back module 204 may determine that if the user averages an additional 167 steps per day (e.g., ⅓ of 500 additional steps per day), consumes an average of 333 calories less per day (e.g., ⅓ of 1000 calories less per day), and averages an additional 20 minutes of sleep per day (e.g., ⅓ of one hour additional sleep per day), the user may receive all of the payment.

The behavior module 206 may specify effects on the future state of the user in terms of one or more behaviors of the user. In these and other embodiments, the effects and their relation to behaviors of the user may be embodied as behavior-based virtual attribute rules that specify a behavior-based virtual attribute based on one or more behaviors of the user. The future state predictor 208 may use the behavior-based virtual attribute rules to determine one or more behavior-based virtual attributes.

An example behavior-based virtual attribute rule may specify that a behavior-based virtual attribute relating to weight loss for the future state is determined according to a formula 5*(a−5,000)/5,000 pounds weight loss, where a is average daily steps of a user for the last month or some other period. Another example behavior-based virtual attribute rule relating to weight loss for the future state may specify one pound weight loss for the future state if the user increases the average daily steps by 10% over a month.

In the foregoing example, the behavior-based virtual attribute rules depend on a single behavior (e.g., steps). In other examples, one or more behavior-based virtual attribute rules may depend on two or more behaviors. For example, behavior-based virtual attribute rules relating to weight loss may depend on steps, caloric intake, hours of sleep per day, and potentially other behaviors.

The future state predictor 208 may receive state data indicative of a current state of the user and estimate a future state of the user from the current state of the user, a behavior-based virtual attribute of the user, and a purchased virtual attribute.

The state data received by the future state predictor 208 may include any health information associated with a user. For example, the state data may include physical health information for a user, such as weight, blood pressure, an average nightly duration of sleep, a cholesterol level, or a fitness state, such as the user's ability to run an eight-minute mile. The state data may also include mental health information for the user including a user's anxiety or stress level. The user may provide the state data manually or the future state predictor 208 may determine the state data from sensor data. For example, the future state predictor 208 may receive sensor data from a GPS sensor or another of the sensors 115 that indicates the user is able to run an eight-minute mile. In another example, the future state predictor 208 may receive a user's cholesterol level from a sensor 115 associated with the user's doctor or a laboratory. In yet another example, the future state predictor 208 may determine the user's anxiety or stress level based on the user's heart rate, a length of time that has elapsed since the user had a panic attack, or as provided by a user. The future state predictor 208 may store the state data as system data 212.

The future state predictor 208 may receive or determine the current state of the user from the system data 212 and/or from another one of the components of the device 200. As an example of the current state of the user, the system data 212 may include a current weight of the user of 170 pounds which may be included in or as the current state of the user.

The future state predictor 208 may apply the behavior-based virtual attribute rules specified by the behavior module 206 to determine the behavior-based virtual attribute of the user. In the example given above, the behavior module 206 specifies the following two behavior-based virtual attribute rules: (1) the weight of the future state is changed by 5*(a−5,000)/5,000 pounds weight loss (where a is the average number of daily steps of the user), and (2) the weight of the future state is reduced by one pound if a increases by 10% over a month. Now suppose that over one month, the user's average daily steps increase from 5,357 steps to 6,000 steps. In this case, a's value is now 6,000 and it increases by 12% ((6,000−5,357)/5,357=0.12=12%). Thus, according to behavior-based virtual attribute rule (1) above, the weight of the future state is reduced by 5*(6,000−5,000)/5,000 pounds=one pound and according to behavior-based virtual attribute rule (2) above, the weight of the future state is reduced by another one pound since a increased by 12%. Accordingly, the future state predictor 208 may determine the behavior-based virtual attribute of the user to be one pound weight loss+one pound weight loss=two pounds weight loss.

On the other hand, suppose the user's average daily steps are only 3,000 steps. In this case, and according to behavior-based virtual attribute rule (1) above, the weight of the future state may be changed by 5*(3,000−5,000)/5,000 pounds=negative two pounds weight loss=two pounds weight gain.

The future state predictor 208 may receive or determine the purchased virtual attribute of the user from the system data 212 and/or from another one of the components of the device 200. Consistent with the example discussed with respect to the earn-back module 204, the future state predictor 208 may receive from the earn-back module 204 or determine from the system data 212 a purchased virtual attribute of three pounds of weight loss.

After the future state predictor 208 receives and/or determines the current state of the user, the behavior-based virtual attribute, and the purchased virtual attribute, the future state predictor 208 may estimate the future state of the user. Continuing with the foregoing examples in which the current state of the user is 170 pounds, the behavior-based virtual attribute is two pounds of weight loss, and the purchased virtual attribute is three pounds of weight loss, the future state predictor 208 may estimate the future state (e.g., future weight) of the user to be 170 pounds−two pounds−three pounds=165 pounds.

After an earn-back time period expires, the associated purchased virtual attribute may be discarded completely, e.g., omitted from future estimations of the future state of the user. Alternatively, all or a portion of the purchased virtual attribute may be included in future estimations of the future state as an earned back virtual attribute, and/or the value of the earned back virtual attribute may decay over time. In these and other embodiments, the future state predictor 208 may estimate the future state of the user based on the current state, the behavior-based virtual attribute, the purchased virtual attribute, and the earned back virtual attribute.

The particular manner in which the earned-back virtual attribute is calculated and handled after expiration of the earn-back time period may be prescribed by one or more earn-back virtual attribute rules which may be applied by the future state predictor 208. An example of an earn-back virtual attribute rule includes calculating at least an initial value of an earned-back virtual attribute as the purchased virtual attribute multiplied by a ratio of an actual behavior change during the corresponding earn-back time period and a behavior change specified for the purchased virtual attribute.

Consider the preceding example in which $15 paid for three pounds of weight loss may be earned back in a month by increasing average daily steps for the month by 500 steps. In this example, the increase of 500 steps is the behavior change specified for the purchased virtual attribute of three pounds of weight loss. Now suppose at the end of the month the user's average daily steps have increased by 400 steps, which is an example of the actual behavior change. According to the foregoing earn back virtual attribute rule, at least the initial value of the earned back virtual attribute corresponding to the purchased virtual attribute of three pounds weight loss is calculated as three pounds weight loss multiplied by the ratio of the actual behavior change (e.g., 400 steps) and the behavior change specified for the purchased virtual attribute (e.g., 500 steps), or three pounds weight loss multiple by 400/500=2.4 pounds weight loss.

The user interface module 210 may generate graphical data for displaying a user interface. In some embodiments, the user interface module 210 may generate a user interface for registering a user by including fields for the user to provide a username, a password, and an option for the user to upload an image of the user that may be used to generate a visualization of a future state of the user.

The user interface may also include fields for the user to specify a type of virtual attribute and a number of virtual attributes for purchase. The type of virtual attribute may be specified manually, from a default list of virtual attributes, etc.

Figure 3A:
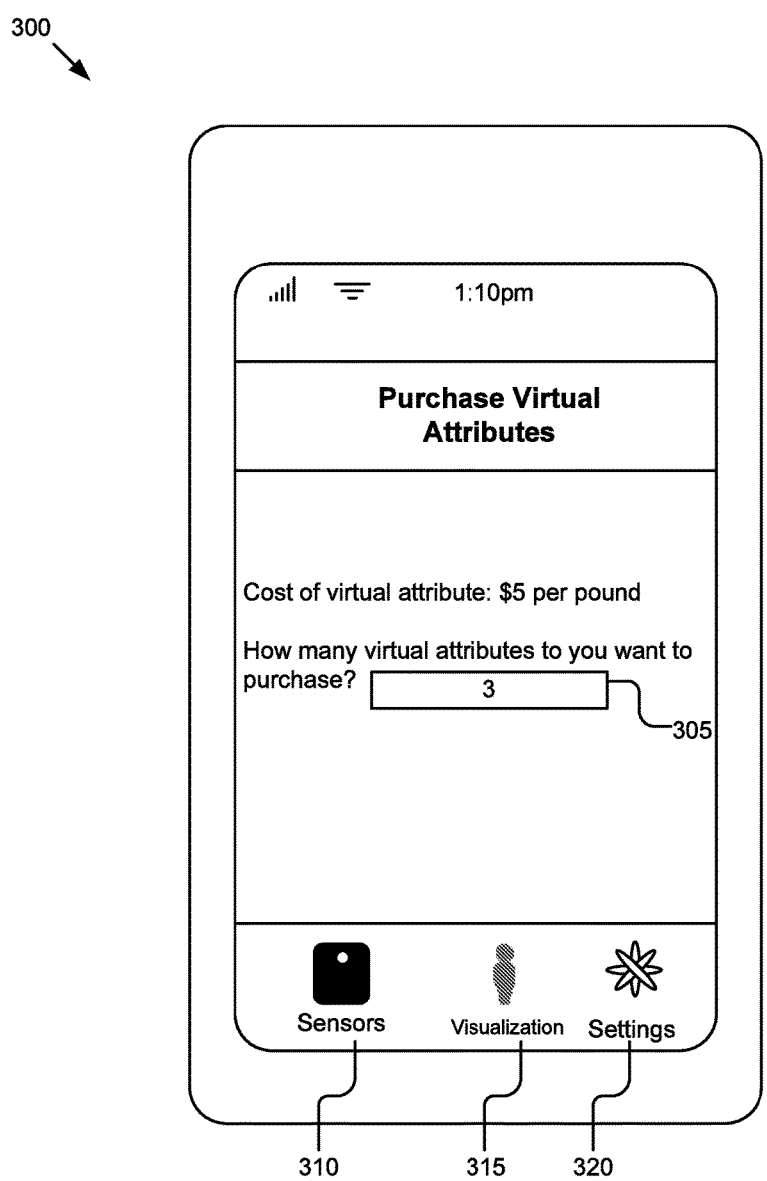
FIG. 3A illustrates an example graphical user interface for a user to define a number of virtual attributes for purchase.

FIG. 3A illustrates an example graphical user interface 300 for a user to define a number of virtual attributes for purchase. The user interface 300 may be designed for a mobile device that prioritizes limited screen space. In this example, the user interface module 210 specifies a cost per unit for a virtual attribute of weight as $5 per pound. The user interface module 210 generates a field 305 for the user to specify a number of virtual attributes for purchase. In this example, the user specifies three pounds for purchase.

The graphical user interface 300 also includes a sensors icon 310 that links to a user interface where the user may configure the health application 111 to receive data from the sensors 115 of FIG. 1. For example, a user may configure the health application 111 to receive step data from a smart watch via Bluetooth, weight data from a scale via a wireless network, etc. The visualization icon 315 may link to a user interface that includes a visualization of a future state of a user as described in greater detail with reference to FIGS. 4A-4C below. The settings icon 320 may link to a user interface that includes settings options.

Figure 3B:
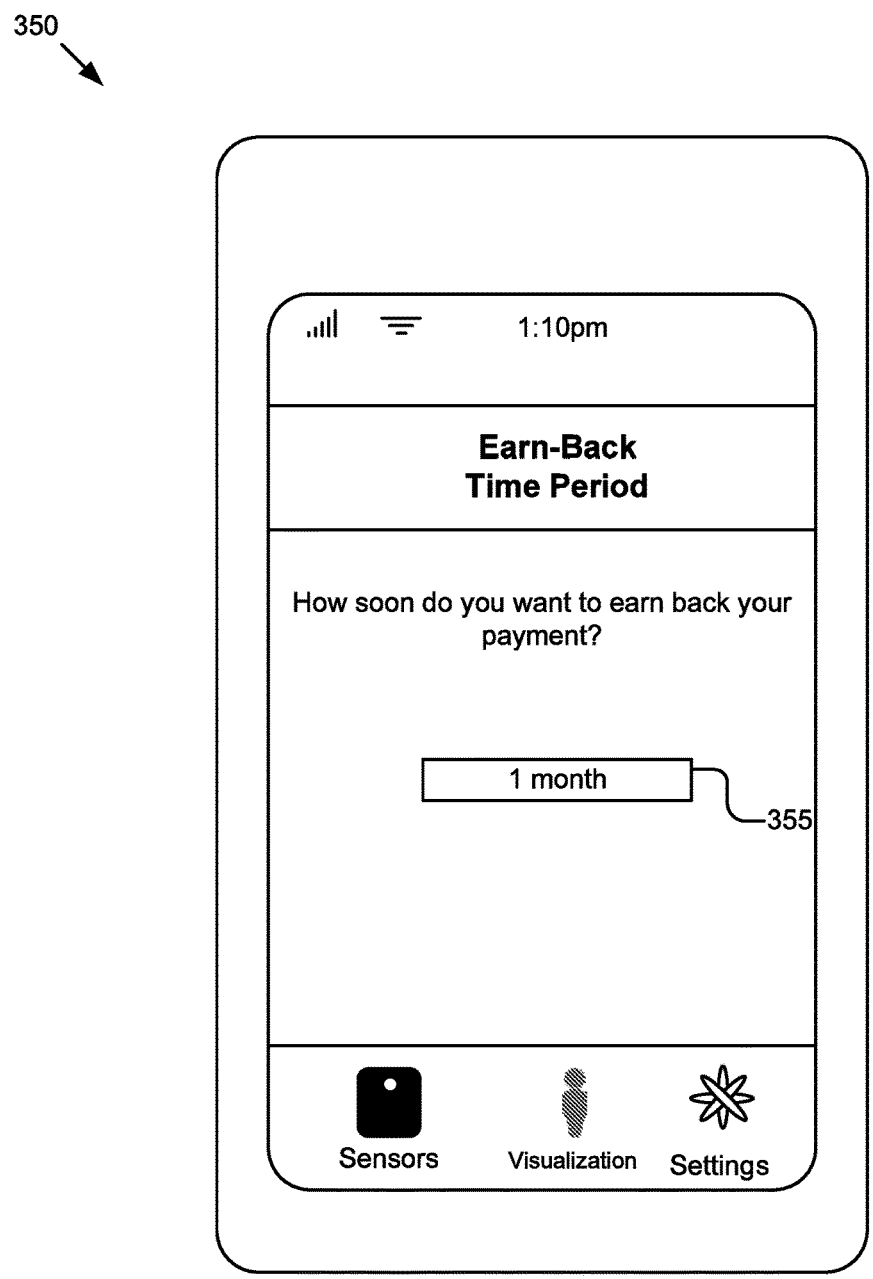
FIG. 3B illustrates an example graphical user interface for a user to configure an earn-back time period.

FIG. 3B illustrates an example graphical user interface 350 for a user to configure an earn-back time period. In some embodiments, the user interface module 210 generates the graphical user interface 350 after a user defines a number of virtual attributes for purchase, for example, by using the graphical user interface 300 in FIG. 3A. The graphical user interface 350 may ask the user to specify an earn-back time period. In this example, the user interface module 210 generates a field 355 where the user may enter a time period. Other embodiments may include a drop down box where the user may select the earn-back time period from a list.

In some embodiments, the user interface module 210 generates graphical data that includes a visualization of the future state of the user to display to the user. The visualization may include a motivational visualization, a warning visualization, or a narrative description.

The user interface module 210 may generate a motivational visualization that includes a rendering of what the user could look like if the user achieves the future state. For example, the motivational visualization may include an avatar of a user as a future state. The user interface module 210 may generate the avatar by receiving an image of a user and converting the image into a cartoon rendering of the user. The user interface module 210 may then modify the image according to a future state. For example, if the future state predictor 208 estimates the future state of a user to be a five-pound weight loss, the motivational visualization may include a slimmer version of the user.

In some embodiments, the user interface module 210 may generate a warning visualization of a future state of the user before the user improves the user's behavior and/or provides a payment. For example, the future state predictor 208 may estimate a warning future state of the user from the current state of the user and the behavior-based virtual attribute of the user. The user interface module 210 may generate a warning visualization of what the user could look like if the user achieves the warning future state in the future. The user may view the warning visualization and decide to improve the user's behavior and/or provide a payment for purchasing a visual attribute.

Figure 4A:
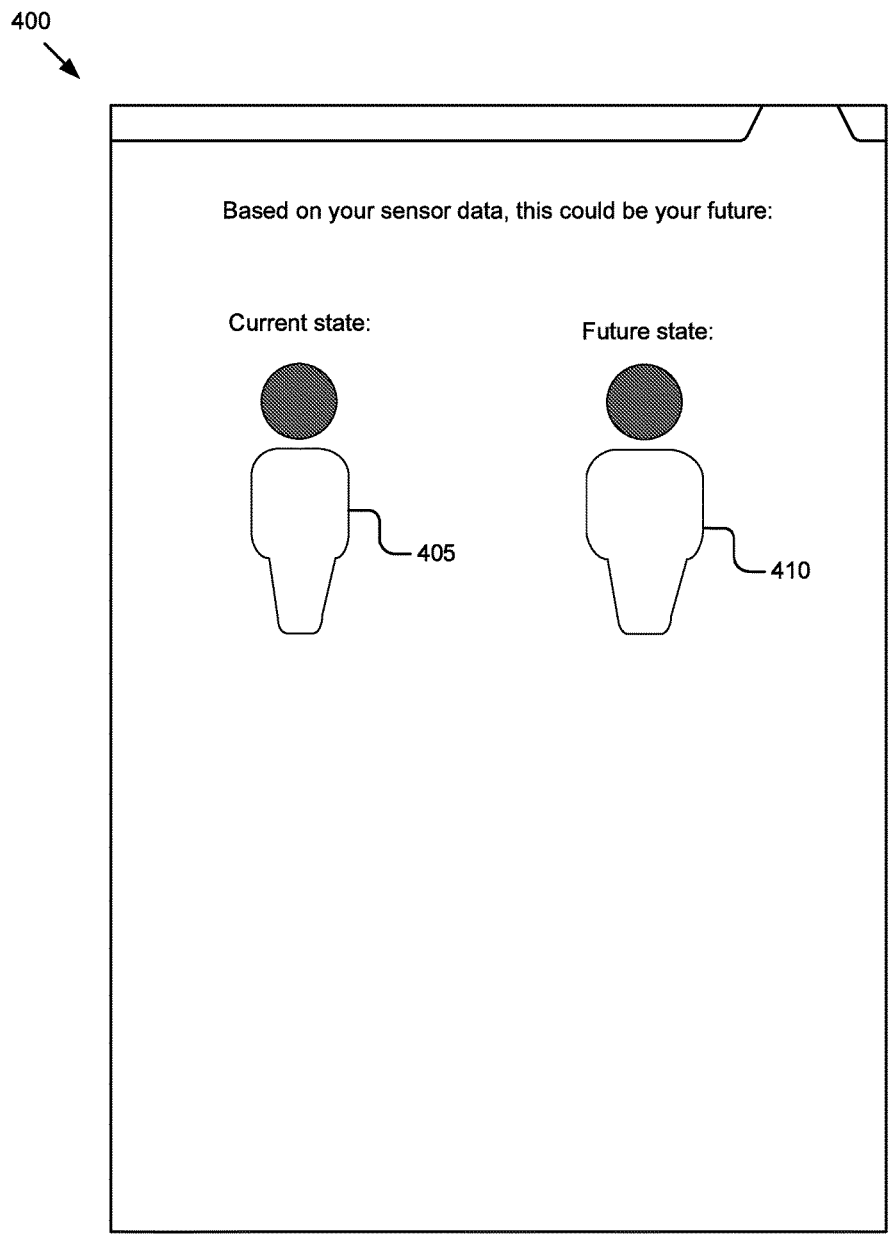
FIG. 4A illustrates an example graphical user interface that includes a warning visualization of what the user could look like if the user achieves a future state.

FIG. 4A illustrates an example graphical user interface 400 that includes a warning visualization of what the user could look like if the user achieves the future state. The graphical user interface 400 may be designed to be displayed in a browser with ample screen space. In this example, the future state predictor 208 may determine that based on the user's sedentary lifestyle, as evidenced by the current state of the user and the behaviors of the user, including historical behaviors of the user, the user may gain five pounds. The user interface module 210 may generate a graphic image of a current state of the user 405 and a warning visualization 410 to illustrate how the user might look in the future with the five-pound weight gain.

The user interface module 210 may generate a motivational visualization of a future state of the user after the user improves the user's behavior and/or provides a payment to purchase a virtual attribute. For example, the future state predictor 208 may estimate a future state of the user from a current state of the user, a behavior-based virtual attribute of the user, a purchased virtual attribute, and optionally an earned-back virtual attribute. The user interface module 210 may generate a motivational visualization of what the user may look like if the user achieves the future state in the future by, e.g., continuing with improved behaviors and/or further improving behaviors to earn back payment for the purchased virtual attribute.

Figure 4B:
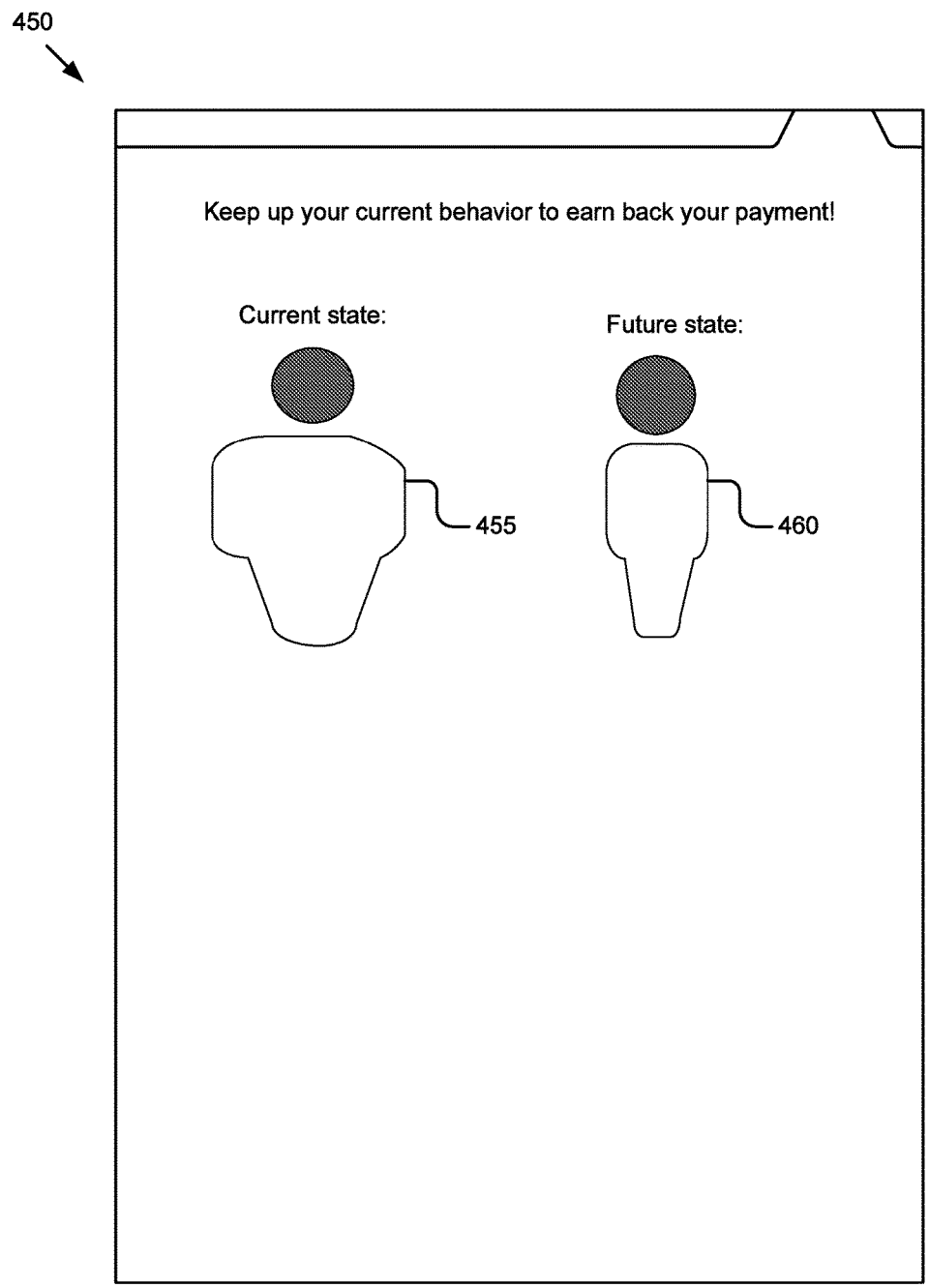
FIG. 4B illustrates an example graphical user interface that includes a motivating visualization of what the user could look like if the user achieves a different future state.

FIG. 4B illustrates an example graphical user interface 450 that includes a motivating visualization of what the user could look like if the user achieves the future state. In this example, the future state predictor 208 may estimate that the future state of the user will weigh 50 pounds less than the current state of the user. The user interface module 210 may generate a graphic image of a current state of the user 455 and a motivational visualization 460 to illustrate how the user might look in the future with the 50-pound weight loss.

In some embodiments, the user interface module 210 may generate a motivational visualization of a user that is enhanced to show a future state. For example, where the virtual attributes include two minutes shaved off of a seven-minute mile, the user interface module 210 may generate a visualization with an enhanced version of the image that includes more defined muscles in the user's calves, less weight around the user's waist, etc. The user may be inspired by the enhanced version of the image because it may be easier for the user to visualize becoming the enhanced version of the image as compared to an avatar of the user.

In some embodiments, the visualization may include a narrative description of future attributes for the user if the user achieves the future state. For example, in the example of the cardiovascular health package that includes a payment for virtual attributes associated with cardiovascular health including weight loss, blood pressure reduction, and cholesterol level improvements, the narrative description may describe an improved weight, an improved blood pressure, an improved cholesterol number, and an estimated life expectancy. In some embodiments, the user interface module 210 may generate a narrative description of future attributes for the user before the user improves the user's behavior and/or before the user purchases virtual attributes. For example, the narrative description may indicate that the user may gain 20 pounds, may have to take blood-pressure medicine, and may have a decreased life expectancy.

Figure 4C:
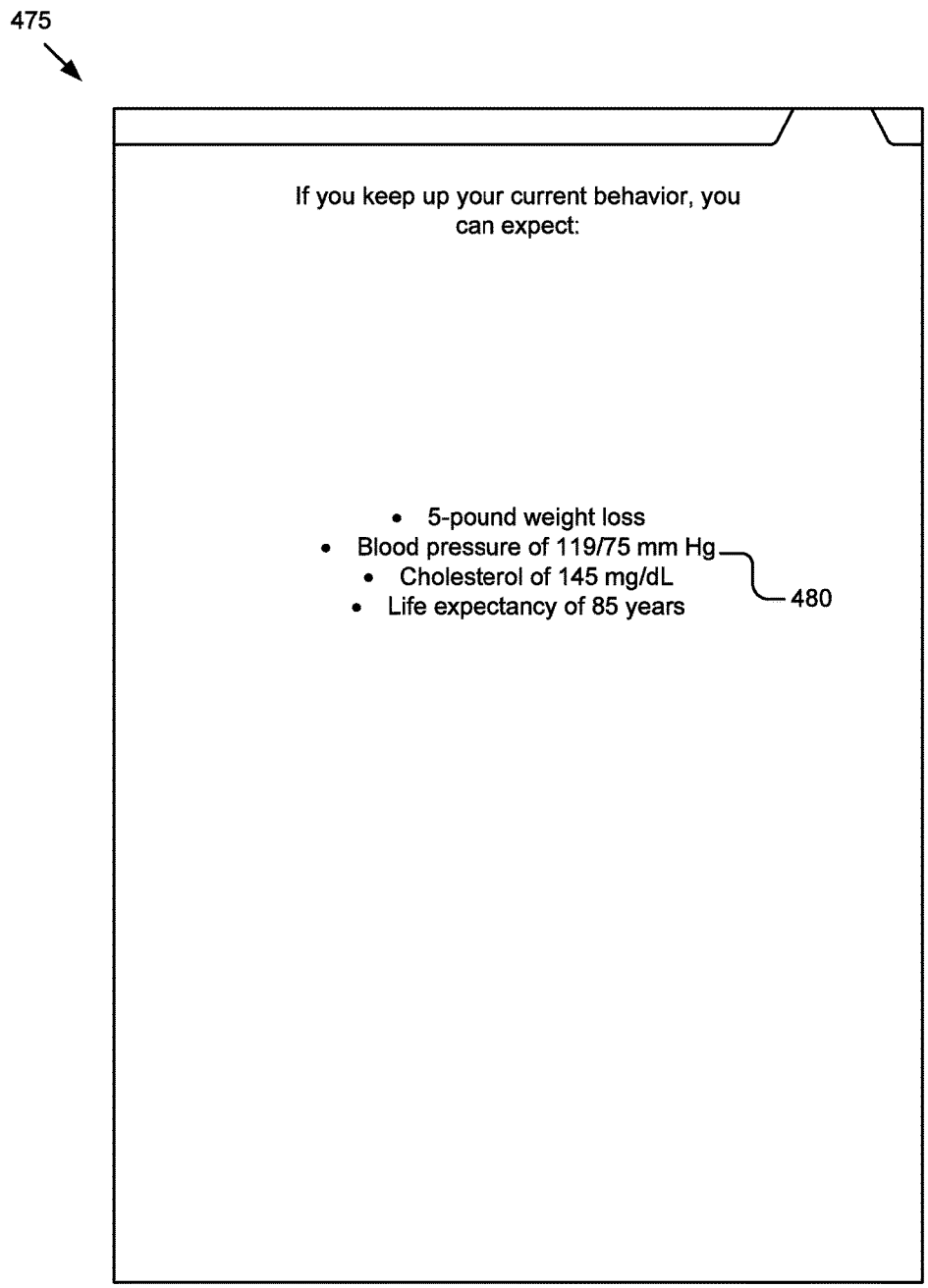
FIG. 4C illustrates an example graphical user interface that includes a narrative description of future attributes for the user if the user achieves the future state.

FIG. 4C illustrates an example graphical user interface 475 that includes a narrative description of future attributes for the user if the user achieves the future state. In this example, the future state predictor 208 may estimate that the future state of the user will weigh five pounds less than the current state, have a blood pressure of 119/75 mmHg, have a cholesterol level of 145 mg/dL, and have an increased life expectancy of 85 years. The user interface module 210 may generate a list 480 of the future attributes determined by the future state predictor 208.

Figure 5:
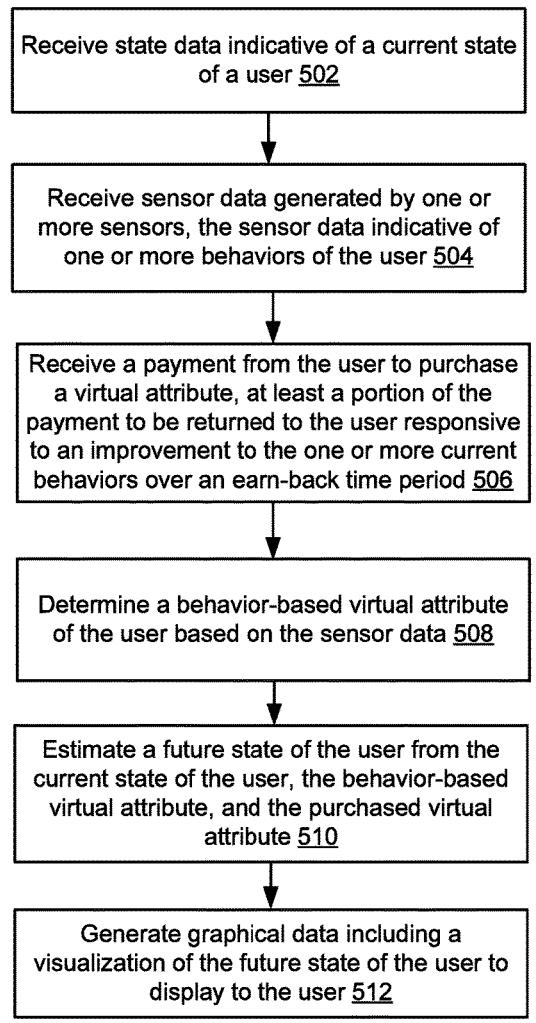
FIG. 5 illustrates a flowchart of an example method to change behavior of a user.

FIG. 5 illustrates a flowchart of an example method 500 to change behavior of a user. The method 500 may be implemented, in whole or in part, by one or more of the health server 101 of FIG. 1, the user device 120 of FIG. 1, the health application 111 of FIG. 1 or 2, the device 200 of FIG. 2, or another suitable device, server, and/or system. The method 500 may begin at block 502.

At block 502, state data indicative of a current state of a user may be received. The health application 111 of FIG. 1 and/or the future state predictor 208 of FIG. 2 may receive state data indicative of the current state of the user. For example, the health application 111 may receive state data indicative of the user's ability to run an eight-minute mile.

At block 504, sensor data generated by one or more sensors may be received where the sensor data is indicative of one or more behaviors of the user. The health application 111 of FIG. 1 and/or the earn-back module 204 of FIG. 2 may receive sensor data generated by one or more sensors 115 of FIG. 1. For example, the health application 111 may receive sensor data that describes that the user runs an average of 8 miles every day. The sensors 115 may include a location sensor, a pedometer, an altimeter, and/or other sensors.

At block 506, a payment may be received from the user to purchase a virtual attribute where at least a portion of the payment is returned to the user responsive to an improvement to the one or more behaviors over an earn-back time period. The health application 111 of FIG. 1 and/or the future state purchaser 202 may receive the payment from the user to purchase the virtual attribute. For example, the virtual attribute may include a reduction of 30 seconds on a time to complete a mile. The user may purchase two 30-second reductions for $10 each for a total of $20.

At block 508, a behavior-based virtual attribute based on the sensor data may be determined by applying a behavior-based virtual attribute rule to the sensor data. The health application 111 of FIG. 1 and/or the future state predictor 208 of FIG. 2 may determine the behavior-based virtual attribute by applying the behavior-based virtual attribute rule to the sensor data. For example, the behavior-based virtual attribute rule may specify that the user reduces a time it takes to run a mile by 30 seconds if the user increases the user's average run of 8 miles a day by two miles, e.g., by running an average of 10 miles a day total.

At block 510, a future state of the user may be estimated from the current state of the user, the behavior-based virtual attribute, and the purchased virtual attribute. The health application 111 of FIG. 1 and/or the future state predictor 208 may estimate the future state of the user from the current state of the user, the behavior-based virtual attribute, and the purchased virtual attribute. For example, the health application 111 may estimate that the future state of user may run a mile 90 seconds faster than the current state of the user that indicates that the user runs an eight-minute mile based on a behavior-based virtual attribute including a 30-second loss on a running time and the purchased virtual attribute including two 30-second reductions.

At block 512, graphical data including a visualization of the future state of the user may be generated to display to the user. The health application 111 of FIG. 1 and/or the user interface module 210 of FIG. 2 may generate graphical data including the visualization of the future state of the user. For example, the health application 111 may generate graphical data including a motivational visualization of the user as an enhanced version of an image of the user that includes more defined muscles in the user's calves, more toned arms, and less weight around the user's waist.

The embodiments described herein may include the use of a special-purpose or general-purpose computer including various computer hardware or software modules, as discussed in greater detail below.

Embodiments described herein may be implemented using computer-readable media for carrying or having computer-executable instructions or data structures stored thereon. Such computer-readable media may include any available media that may be accessed by a general-purpose or special-purpose computer. By way of example, and not limitation, such computer-readable media may include non-transitory computer-readable storage media including random access memory (RAM), read-only memory (ROM), electrically erasable programmable read-only memory (EE-PROM), compact disc read-only memory (CD-ROM) or other optical disk storage, magnetic disk storage or other magnetic storage devices, flash memory devices (e.g., solid state memory devices), or any other storage medium which may be used to carry or store desired program code in the form of computer-executable instructions or data structures and which may be accessed by a general-purpose or special-purpose computer. Combinations of the above may also be included within the scope of computer-readable media.

Computer-executable instructions may include, for example, instructions and data which cause a general-purpose computer, special-purpose computer, or special-purpose processor device (e.g., one or more processors) to perform a certain function or group of functions. Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

As used herein, the terms "module" or "component" may refer to specific hardware embodiments configured to perform the operations of the module or component and/or software objects or software routines that may be stored on and/or executed by general-purpose hardware (e.g., computer-readable media, processor devices, etc.) of the computing system. In some embodiments, the different components, modules, engines, and services described herein may be implemented as objects or processes that execute on the computing system (e.g., as separate threads). While some of the system and methods described herein are generally described as being implemented in software (stored on and/or executed by general-purpose hardware), specific hardware embodiments or a combination of software and specific hardware embodiments are also possible and contemplated. In this description, a "computing entity" may be any computing system as previously defined herein, or any module or combination of modulates running on a computing system.

All examples and conditional language recited herein are intended for pedagogical objects to aid the reader in understanding the invention and the concepts contributed by the inventor to furthering the art, and are to be construed as being without limitation to such specifically recited examples and constraints. Although embodiments of the present inventions have been described in detail, it should be understood that the various changes, substitutions, and alterations could be made hereto without departing from the spirit and scope of the invention.

What is claimed is:

1. A method to change a behavior of a user, the method comprising:
   receiving state data indicative of a current state of the user;
   receiving sensor data generated by one or more hardware sensors, the sensor data indicative of one or more behaviors of the user;
   receiving payment from the user to purchase data representative of a virtual attribute, at least a portion of the payment to be returned to the user responsive to an improvement to the one or more behaviors over an earn-back time period;
   determining a behavior-based virtual attribute of the user based on the sensor data, by applying one or more behavior-based virtual attribute rules to the sensor data;
   estimating a future state of the user by subtracting a value associated with the behavior-based virtual attribute and a value associated with the purchased data representative of the virtual attribute from a value associated with the current state of the user; and
   generating graphical data including a visualization of the future state of the user to display to the user, the visualization including a motivational visualization of what the user could look like if the user achieves the future state.

2. The method of claim 1, further comprising determining a cost, in terms of the sensor data generated by the one or more hardware sensors, for the user to earn back an amount of the payment associated with the purchased data representative of the virtual attribute; and
   wherein for the user to earn back at least part of the amount of the payment, the sensor data indicates an actual behavior change within the earn-back time period that contributes to the improvement to the one or more behaviors.

3. The method of claim 1, wherein the visualization further includes
   a narrative description of future attributes for the user if the user achieves the future state in the future.

4. The method of claim 1, wherein determining the behavior-based virtual attribute of the user based on the sensor data comprises mapping an actual behavior of the one or more behaviors of the user indicated by the sensor data to the behavior-based virtual attribute and to a value of the behavior-based virtual attribute.

5. The method of claim 1, wherein the sensor data includes historical data indicative of one or more historical behaviors of the user.

6. The method of claim 5, further comprising
   displaying graphical data including a warning visualization of what the user could look like if the user achieves a warning future state of the user in the future.

7. The method of claim 1, wherein the purchased data representative of the virtual attribute includes a package of data representative of multiple virtual attributes that are aimed at improving a health condition, wherein the data representative of the multiple virtual attributes correspond to the sensor data.

8. The method of claim 1, further comprising determining a target behavior change that contributes to the improvement to the one or more behaviors of the user that would result in the user earning back the payment over the earn-back time period.

9. The method of claim 8, further comprising:
   receiving the sensor data generated by the one or more hardware sensors, the sensor data indicative of an actual behavior change of the user that contributes to the improvement to the one or more behaviors;
   determining a ratio of the actual behavior change to the target behavior change;
   determining a value of the at least the portion of the payment based on the ratio; and
   returning the determined value to the user.

10. The method of claim 9, wherein:
    the ratio is one if the actual behavior change is greater than or equal to the target behavior change;
    the ratio is between zero and one if the actual behavior change is less than the target behavior change; and
    determining the value based on the ratio comprises multiplying the payment by the ratio.

11. The method of claim 1, wherein estimating the future state of the user from the current state of the user is based on a future time period that is longer than the earn-back time period.

12. The method of claim 1, wherein the one or more hardware sensors include one or more of: a pedometer, a scale, a sleep sensor, a location sensor, a blood pressure monitor, a pulse oximeter, a cholesterol monitoring device, a heart rate monitor, and an altimeter.

13. The method of claim 1, further comprising providing the graphical data to a user device associated with the user, the user device including one or more of a mobile device, a smart watch, and a wearable device.

14. A non-transitory computer-readable medium that includes computer-readable instructions stored thereon that are executable by a processor to perform or control performance of operations comprising:
    receiving state data indicative of a current state of the user;
    receiving sensor data generated by one or more hardware sensors, the sensor data indicative of one or more behaviors of the user;
    receiving payment from the user to purchase data representative of a virtual attribute, at least a portion of the payment to be returned to the user responsive to an improvement to the one or more behaviors over an earn-back time period;
    determining a behavior-based virtual attribute of the user based on the sensor data, by applying one or more behavior-based virtual attribute rules to the sensor data;

estimating a future state of the user by subtracting a value associated with the behavior-based virtual attribute and a value associated with the purchased data representative of the virtual attribute from a value associated with the current state of the user; and generating graphical data including a visualization of the future state of the user to display to the user, the visualization including a motivational visualization of what the user could look like if the user achieves the future state.

15. The non-transitory computer-readable medium of claim 14, wherein the operations further comprise:

determining a cost, in terms of the sensor data generated by the one or more hardware sensors, for the user to earn back an amount of the payment associated with the purchased data representative of the virtual attribute; and wherein for the user to earn back at least part of the amount of the payment, the sensor data indicates an actual behavior change within the earn-back time period that contributes to the improvement to the one or more behaviors.

16. The non-transitory computer-readable medium of claim 14, wherein the visualization further includes a narrative description of future attributes for the user if the user achieves the future state in the future.

17. The non-transitory computer-readable medium of claim 14, wherein the operations further comprise determining a target behavior change that contributes to the improvement to the one or more behaviors of the user that would result in the user earning back the payment over the earn-back time period.

18. The non-transitory computer-readable medium of claim 17, wherein the operations further comprise:

receiving the sensor data generated by the one or more hardware sensors, the sensor data indicative of the actual behavior change of the user that contributes to the improvement to the one or more behaviors;

determining a ratio of the actual behavior change to the target behavior change;

determining a value of the at least the portion of the payment based on the ratio; and returning the determined value to the user.

19. The non-transitory computer-readable medium of claim 18, wherein:

the ratio is one if the actual behavior change is greater than or equal to the target behavior change;

the ratio is between zero and one if the actual behavior change is less than the target behavior change; and determining the value based on the ratio comprises multiplying the payment by the ratio.

20. The non-transitory computer-readable medium of claim 14, wherein estimating the future state of the user from the current state of the user is based on a future time period that is longer than the earn-back time period.

* * * * *